(12) United States Patent
Hille et al.

(10) Patent No.: US 6,194,404 B1
(45) Date of Patent: Feb. 27, 2001

(54) PROCESS FOR THE ISOLATION OF GALANTHAMINE

(75) Inventors: Thomas Hille; Hans-Rainer Hoffmann, both of Neuwied; Mirko Kreh; Rudolf Matusch, both of Marburg, all of (DE)

(73) Assignee: LTS Lohmann Therapie-Systeme GmbH, Neuwied (DE)

( * ) Notice: Subject to any disclaimer, the term of this patent is extended or adjusted under 35 U.S.C. 154(b) by 0 days.

(21) Appl. No.: 09/130,883

(22) Filed: Aug. 7, 1998

Related U.S. Application Data

(62) Division of application No. 08/913,461, filed as application No. PCT/EP96/01094 on Mar. 14, 1996, now Pat. No. 5,877,172.

(30) Foreign Application Priority Data

Mar. 17, 1995 (DE) .............................. 195 09 663

(51) Int. Cl.$^7$ ............................ A01N 43/46; A61K 31/55
(52) U.S. Cl. ............................................... 514/215
(58) Field of Search .............................. 514/715

(56) References Cited

U.S. PATENT DOCUMENTS

| 4,663,318 | * | 5/1987 | Davis | 514/215 |
| 5,336,675 | * | 8/1994 | Snorrason | 514/215 |
| 5,428,159 | * | 6/1995 | Shieh et al. | 540/215 |
| 5,519,017 | * | 5/1996 | Opitz | 514/215 |

FOREIGN PATENT DOCUMENTS

| 1193061 | * | 5/1965 | (DE) . |
| WO 94/16708 | * | 8/1994 | (WO) . |

OTHER PUBLICATIONS

Abstract to Moormann et al. of WO 94/16708 A1 Aug. 4, 1994.*
Bastida et al., "Alkaloids from Narcissus confusus", Phytochemistry, vol. 26, No. 5, pp. 1519–1524, 1987.*
Abstract to Kramarenko of Pharmaceuticals, vol. 82, No. 64386f, pp.463–464, 1975.*
Chem. Abstracts vol. 82, cit# 64386f, Kramarenko, 1975.*
Chem. Abstracts vol. 66, cit# 88630b, Stom, 1967.*
Pharmazie 38, pp 596–600, 1983.*
Phytochemistry, vol. 26, No. 5, pp. 1519–1524, 1987.*

* cited by examiner

Primary Examiner—Dwayne C. Jones
(74) Attorney, Agent, or Firm—Wenderoth, Lind & Ponack, L.L.P.

(57) ABSTRACT

The subject matter of the present invention concerns a process for the isolation of the alkaloid galanthamine; the galanthamine itself which has been produced according to this process; the use of the galanthamine thus produced in galenic preparations; and the galanthamine thus produced for treating narrow-angle glaucoma, Alzheimer's disease, as well as alcohol and nicotine dependence.

21 Claims, 2 Drawing Sheets

PROCESS FOR THE ISOLATION OF GALANTHAMINE

This application is a division of application Ser. No. 08/913,461, filed Jan. 12, 1998, now U.S. Pat. No. 5,877,172, which application is a U.S. National Phase application of International Application No. PCT/EP96/01094, filed Mar. 14, 1996.

The present invention relates to a process for isolating the alkaloid galanthamine; the galanthamine itself which has been produced by this process; the use of galanthamine thus manufactured in galenic preparations; as well as to galanthamine thus produced for the treatment of narrow-angle glaucoma, Alzheimer's disease, as well as alcohol and nicotine dependence.

Galanthamine (4a, 5, 9, 10, 11, 12-hexahydro-3-methoxy-11-methyl-6 H-benzofuro-(3a, 3, 2-ef)-(2) benzazepine-6-ol) is a tetracyclic alkaloid which, owing to its pharmacological properties, belongs to the group of reversibly acting cholinesterase inhibitors. Its effects are similar to those of physostigmine and neostigmine. However, it also has unique specific properties, for example, highly analgesic effects comparable to those of morphine. As a cholinesterase inhibitor the therapeutic range of galanthamine is three to six times broader, since it is not as toxic as physostigmine and neostigmine. This advantage compensates for its slightly lower cholinesterase-inhibiting action, relative to dosage. Galanthamine is used in poliomyelitis and different diseases of the nervous system, but mainly in the treatment of narrow-angle glaucoma and as antidote after curare applications. The use of galanthamine in the treatment of Alzheimer's disease is in an experimental stage. Lately, the treatment of alcohol and nicotine dependence has also been described (DE-OS 40 10 079, DE-OS 43 01 782).

The therapy of Alzheimer's disease, alcohol and nicotine dependence, as well as that of narrow-angle glaucoma requires long-acting drug forms adapted to the particular circumstances. This could be an eye ointment in the treatment of narrow-angle glaucoma. In the treatment of Alzheimer's disease, alcohol or nicotine dependence, complicated therapeutic plans or prolonged infusions are unsuitable for obvious reasons. In these diseases, a transdermal therapeutic system (TTS) is a suitable form, for example that described in DE-OS 43 01 783. Neither the intact skin nor the cornea permit absorption of active substance salts. For this reason it is not possible to use galanthamine hydrobromide or galanthamine hydrochloride with ointments or a TTS in the therapy of narrow-angle glaucoma, Alzheimer's disease, or alcohol or nicotine dependence. The pure galanthamine base must therefore be used.

An economically efficient synthesis of galanthamine base is not possible because of its complicated tetracyclic structure with three optically active carbon atoms. For this reason, galanthamine is usually isolated from plants belonging to Amaryllidaceae, for example, from galanthus species, such as the snowdrop or Leucojum aestivum. These plants have the advantage of comprising galanthamine in concentrations of up to 0.3% with only small amounts of companion alkaloids so that the extraction method described in DE-PS 11 93 061 can be used. However, both the galanthus species and Leucojum aestivum are protected. On the other hand, the extraction method described in DE-PS 11 93 061 preferably uses chlorohydrocarbons which have fallen into discredit for toxicological reasons. The Pharmacopoeias of the Western World therefore call for a limitation of the residual chlorohydrocarbon content to <10 ppm. In the preparation of drugs chlorohydrocarbons should therefore be avoided as far as possible. Moreover, in the known process, the solvent extract must be adsorbed to alumina to ensure separation of the resinous substances and companion alkaloids. From the solution obtained after filtering off the alumina, the galanthamine is then purified by galanthamine hydrobromide; this involves disposal of halogen salts. For the use in ointments or in a TTS, the galanthamine base must then additionally be liberated from this galanthamine hydrobromide.

It is accordingly the object of the present invention to provide a process for the isolation and purification of galanthamine, which does not have the drawbacks of the prior art processes. In particular, purification is to be facilitated, the use of chlorohydrocarbons and purification by means of galanthamine salts are to be avoided. The object is achieved according to the present invention by a process having the characterizing features of as described herein. Preferred embodiments are further disclosed.

In detail, the subject matter of the present invention is a process for the isolation of galanthamine from biological material which is recovered from agriculturally cultivated amaryllidacea species or from those which are commonly regarded as "weeds" and are not protected, preferably from the bulbs of these plants. These amaryllidaceae include, for example, narcissi or crinum species. Particularly suitable are Narcissus pseudonarcissus "Carlton" or the Asian climber Crinum amabile. Although these plants only have a tenth of the galanthamine amount contained in the protected plants, and, moreover, have up to twelve companion alkaloids, the process according to the present invention surprisingly makes it possible to isolate galanthamine base therefrom with a purity suitable for the use in drugs.

Figure 2:
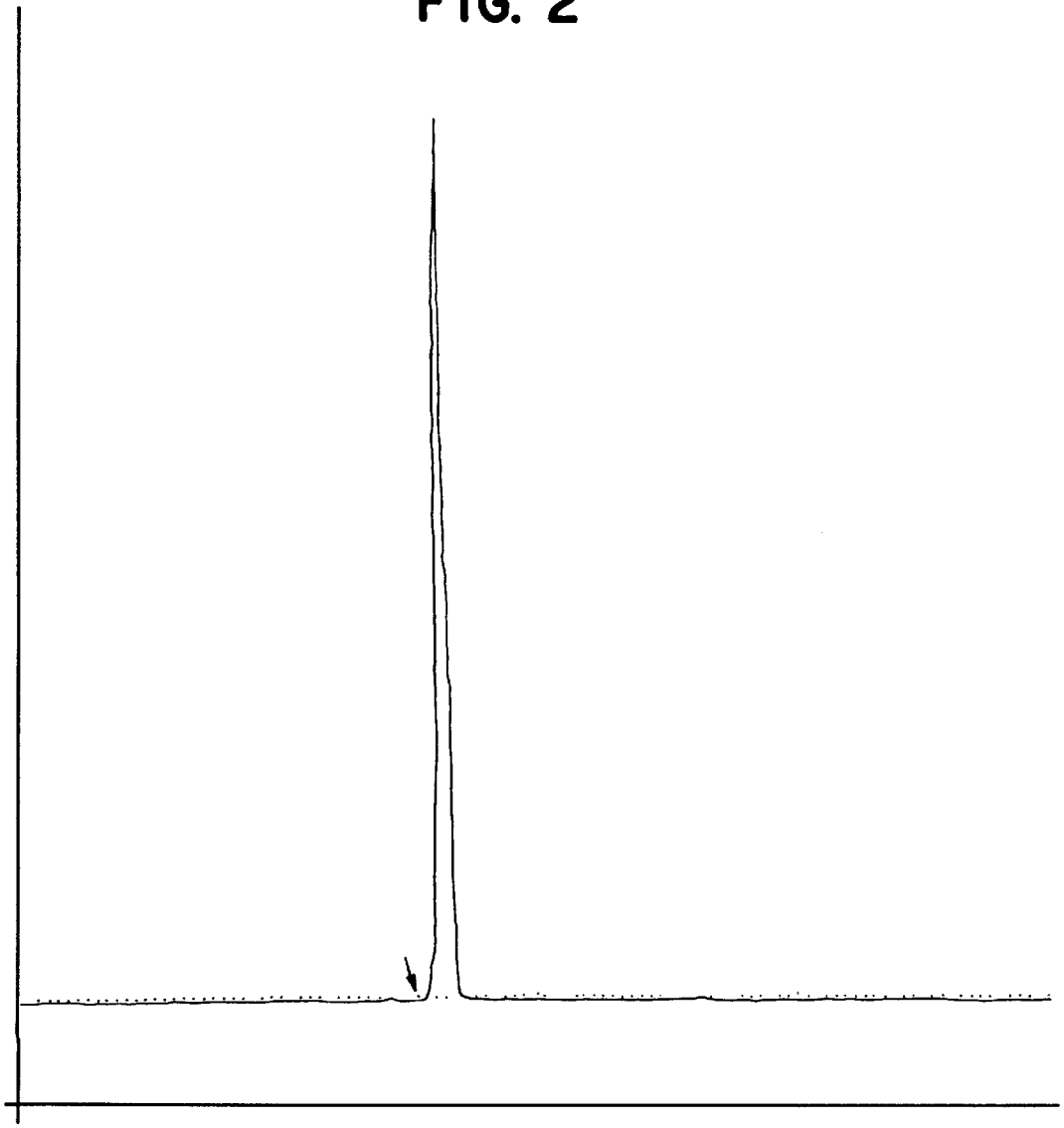
FIG. 2 is an HPLC-chromatogram of the galanthamine product of Example 3.

According to the present invention galanthamine-containing, biological material, which is preferably comminuted and mixed with alkali powder, preferably with sodium hydroxide pellets, soda, potash, or similar salts suitable to liberate bases from biological material and to prepare pharmacological active substances, is extracted with toxicologically safe organic solvents, and the galanthamine from this extract is purified by means of liquid-liquid extraction. It is particularly important for the success of the process according to the present invention to maintain the pH-value in the first stage of the liquid-liquid extraction. The liquid-liquid extraction is carried out in a first stage at a pH of about 4, and in a second stage at a pH of about 9. In addition to concentrated ammonia, soda solution of another base may be used to adjust the pH-value. Diethyl ether or special boiling-point gasoline is used as toxicologically safe organic solvent. Special boiling-point gasoline is preferably used, with it a certain preliminary purification can be achieved. The solvent is removed, and galanthamine is recrystallized from a suitable solvent, preferably from isopropanol. The white galanthamine base having a melting point of 129 to 130° C. is obtained. The purity of the galanthamine thus obtained is shown in the HPLC-chromatogram (FIG. 2). The purity of the galanthamine is $\geq 99\%$.

This result is very amazing since the process according to DE-PS 11 93 061 used so far was found to be unsuitable to isolate galanthamine from biological material containing small amounts of galanthamine and up to 12 companion alkaloids. The process described in DE-PS 11 93 061 results in an emulsion which cannot be broken so that an extraction is rendered impossible. A slightly modified process resulted in an oily residue which, according to HPLC-chromatogram (FIG. 1), is contaminated by at least four substances.

It must therefore be regarded as a particular surprise that the free galanthamine base can be isolated in pure form and good yield from biological material comprising small amounts of galanthamine in addition to a large number of companion alkaloids by means of the simple process according to the present invention, without having to carry out an additional adsorption step to aluminum oxide.

The galanthamine base produced according to the present invention may be used for the treatment of narrow-angle glaucoma, Alzheimer's disease, or alcohol and nicotine dependence. In addition, the galanthamine base produced according to the present invention may be used in galenic preparations, such as ophthalmic ointments or transdermal therapeutic systems, which may also be used to treat the above-mentioned diseases.

The present invention is more particularly described in the examples that follow, which are intended to illustrate, but not to limit, the present invention:

EXAMPLE 1
(Comparison):

In accordance with the process described in DE-PS 11 93 061, 10 kg air-dried, comminuted bulbs of Narcissus pseudonarcissus "Carlton" is carefully mixed with 2.5 l of a 8% aqueous ammonia solution. The material swells; the whole batch pastes up. The addition of 23 l dichloroethane intended for extraction results in an emulsion which cannot be broken.

Figure 1:
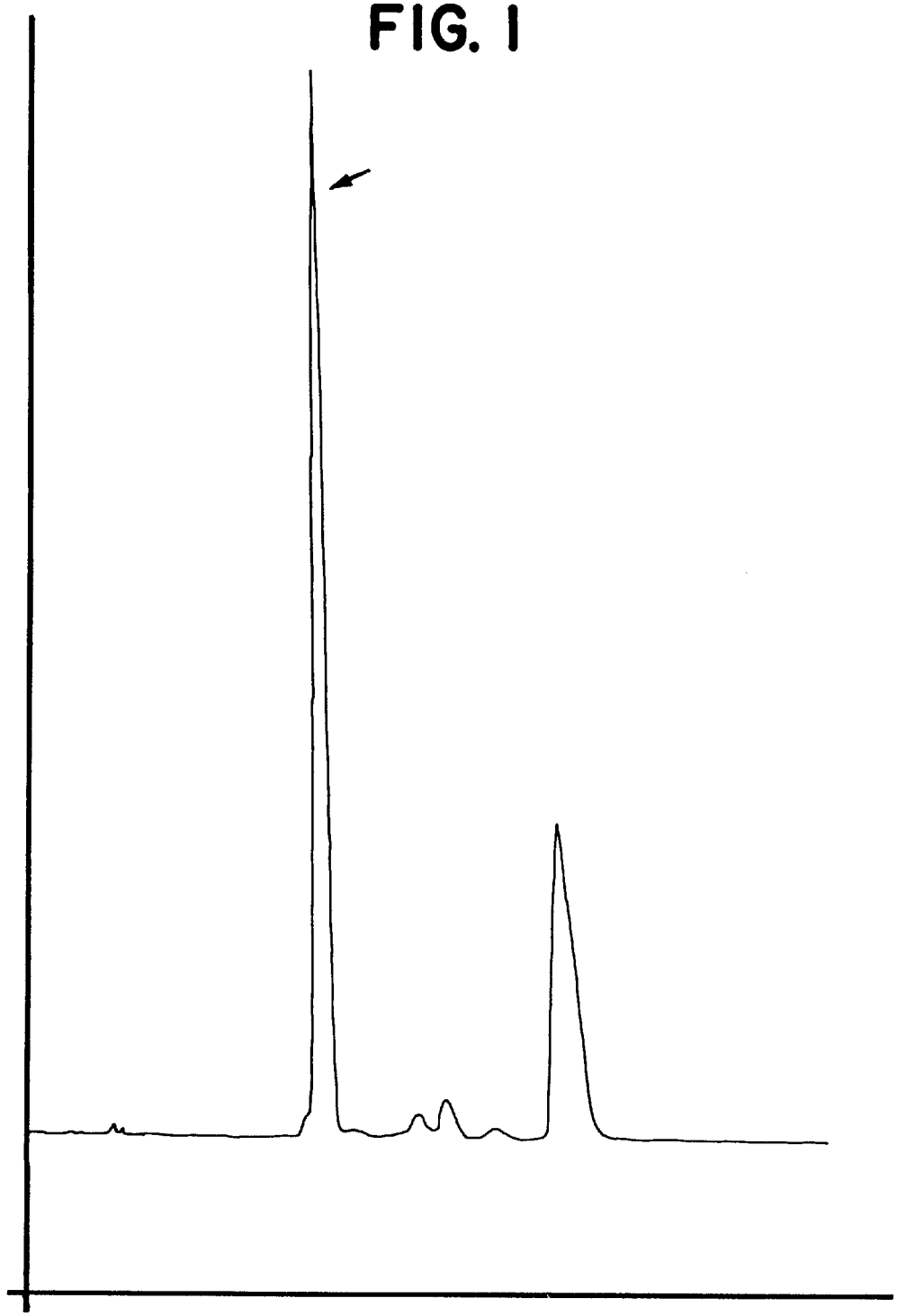
FIG. 1 is an HPLC-chromatogram of the oily residue obtained in Example 2.

EXAMPLE 2
(Comparison):

The process for the isolation of galanthamine known in the art (DE-PS 11 93 061) is modified. 10 kg air-dried, comminuted bulbs of Narcissus pseudonarcissus "Carlton" is carefully mixed with 400 g sodium carbonate. 23 l dichloroethane is added. The mixture is allowed to stand for 10 hours; then the solvent is decanted. The bulbs are once again doused with 23 l dichloroethane which is decanted after 2 to 3 hours. After that, 17 l dichloroethane is added to the bulbs for the third time; however, this is decanted immediately. The mixed dichloroethane extracts are extracted by means of 10% sulfuric acid (2×600 ml each; 2×300 ml each). The acidic extracts are mixed and purified from traces of dichloroethane by means of shaking out with diethyl ether. Under stirring and cooling to 15 to 20° C., about 200 ml of a 25% aqueous ammonia solution is then added up to alkaline litmus reaction. The pH is in the range of 7 to 8. Different from the indications in the art, the companion alkaloids do not precipitate. The alkaline solution is saturated with salt and extracted with diethyl ether. After evaporation of the ether, a negligible residue remains, which is also different from the indications in the art. The pH-value of the aqueous phase is set to about 14 by saturating it with potash. The aqueous phase is repeatedly extracted with diethyl ether. The mixed ether extracts are evaporated to dryness, the remaining galanthamine-containing residue is dissolved in acetone (50 ml). In contrast to the art, there is no precipitate. 350 ml acetone is replenished, 200 g aluminum oxide is added, and stirring is effected for 45 minutes. The aluminum oxide is filtered off and washed twice with 100 ml acetone each time. The mixed acetone solutions are evaporated to dryness. 1.3 g of an oily residue is obtained which is examined by means of HPLC. The chromatogram is shown in FIG. 1. The main peak, the galanthamine, is marked. It is clearly visible that the galanthamine thus isolated is contaminated by at least four substances.

EXAMPLE 3

100 kg air-dried, comminuted bulbs of Narcissus pseudonarcissus "Carlton" is carefully mixed with 4 kg of sodium carbonate. The mixture is divided into three equal parts, and each is doused with 15 l special boiling-point gasoline 80/110. The mixtures are allowed to stand for 24 hours. The solvents are each renewed twice, collected, and evaporated to dryness in low vacuum. The extracts are placed in 2% aqueous sulfuric acid and adjusted to a pH of 4 with concentrated aqueous ammonia solution. Five extractions with diethyl ether follow. The aqueous phase is set to a pH of 9 with concentrated ammonia and extracted five times with diethyl ether. These ether fractions are collected, dried with sodium sulfate, and evaporated. 20 g of a slightly yellow, oily residue is obtained, which is recrystallized from hot isopropanol. 10 g of white galanthamine base having a melting point of 129–130° C. is obtained. Only one peak is visible in the HPLC chromatogram (FIG. 2).

What is claimed is:

1. A pharmaceutically emoloyable galanthamine having a purity of >99% as show by HPLC and being produced according to a process wherein
   a galanthamine-containing, biological material is extracted with a toxicologically safe organic solvent and the galanthamine from this extract is purified by means of liquid-liquid extraction, said liquid-liquid extraction being carried out in the first stage at a pH-value of about 4.

2. The galanthamine according to claim 1, wherein the biological material is comminuted and mixed with alkali powder prior to the extraction.

3. The galanthamine according to claim 2, wherein the alkali powder is sodium carbonate.

4. The galanthamine according to claim 1, wherein the liquid-liquid extraction is carried out in a second stage at a pH-value of about 9.

5. The galanthamine according to claim 1, wherein the toxicologically safe organic solvent is diethyl ether or special boiling point gasoline.

6. The galanthamine according to claim 5, wherein the toxicologically safe organic solvent is special boiling-paint gasoline.

7. The galanthamine according to claim 1, wherein the galanthamine is recrystallized from a suitable solvent.

8. The galanthamine according to claim 7, wherein the suitable solvent is isopropanol.

9. The galanthamine according to claim 1, wherein the biological material is plant parts of amaryllidaceae.

10. The galanthamine according to claim 9, wherein the plant parts are bulbs.

11. The galanthamine according to claim 9, wherein the amaryllidaceae is a narcissi species or crinum species.

12. The galanthamine according to claim 11, wherein the narcissi species is narcissus pseudonarcissus "Carlton", and the crinum species is Crinum amabile.

13. A galenic administration form containing galanthamine as defined in claim 1.

14. An ophthalmic ointment containing galanthamine as defined in claim 1.

15. A transdermal therapeutic system containing galanthamine as defined in claim 1.

16. A method for the treatment of narrow-angle glaucoma which comprises administering to a patient in need of such treatment an effective amount of galanthamine as defined in claim 1.

17. A method for the treatment of Alzheimer's disease which comprises administering to a patient in need of such treatment an effective amount of galanthamine as defined in claim 1.

18. A method for the treatment of alcohol dependence which comprises administering to a patient in need of such treatment an effective amount of galanthamine as defined in claim 1.

19. A method for the treatment of nicotine dependence which comprises administering to a patient in need of such treatment an effective amount of galanthamine as defined in claim 1.

20. A pharmaceutical preparation which comprises an effective amount of galanthamine as defined in claim 1 and at least one pharmaceutical adjuvant.

21. The pharmaceutical preparation according to claim 21 in a topical application form.

* * * * *